United States Patent [19]

Hamada et al.

[11] Patent Number: 4,791,054
[45] Date of Patent: * Dec. 13, 1988

[54] HEAT EXCHANGER AND BLOOD OXYGENATING DEVICE FURNISHED THEREWITH

[75] Inventors: Eiichi Hamada; Toshio Yoshihara; Atushi Nakashima; Jun Kamo, all of Otake, Japan

[73] Assignee: Mitsubishi Rayon Co., Ltd., Tokyo, Japan

[*] Notice: The portion of the term of this patent subsequent to Jan. 27, 2004 has been disclaimed.

[21] Appl. No.: 939,236

[22] Filed: Dec. 8, 1986

Related U.S. Application Data

[63] Continuation of Ser. No. 699,910, Feb. 8, 1985, abandoned.

[30] Foreign Application Priority Data

Oct. 1, 1984 [JP] Japan .................. 59-205895
Oct. 2, 1984 [JP] Japan .................. 59-206531
Oct. 8, 1984 [JP] Japan .................. 59-210948

[51] Int. Cl.⁴ .................. A61M 1/03; A61M 1/14
[52] U.S. Cl. .................. 435/2; 422/46; 422/48; 128/DIG. 3; 210/321.3; 210/321.4; 210/321.8; 165/160
[58] Field of Search .................. 422/46, 48; 55/158; 128/DIG. 3; 210/321.3, 321.4; 435/2; 165/160, 161

[56] References Cited

U.S. PATENT DOCUMENTS

| | | | |
|---|---|---|---|
| 3,998,593 | 12/1976 | Yoshida et al. | 422/48 X |
| 4,188,360 | 2/1980 | Kurata | 422/46 |
| 4,239,729 | 12/1980 | Hasegawa et al. | 128/DIG. 3 X |
| 4,272,373 | 6/1981 | Stenberg et al. | 422/48 X |
| 4,374,802 | 2/1983 | Fukasawa | 210/321.3 X |
| 4,376,095 | 3/1983 | Hasegawa | 422/46 |
| 4,428,403 | 1/1984 | Lee et al. | 422/46 X |
| 4,622,206 | 11/1986 | Torgeson | 422/48 |
| 4,639,353 | 1/1987 | Takemura et al. | 422/48 X |
| 4,657,743 | 4/1987 | Kanno | 422/46 |
| 4,659,549 | 4/1987 | Hamada et al. | 422/48 |

FOREIGN PATENT DOCUMENTS 0003495 12/1978 European Pat. Off. .
0046583 8/1981 European Pat. Off. .
8100297 7/1979 PCT Int'l Appl. .
1467508 3/1977 United Kingdom .

Primary Examiner—Michael S. Marcus
Assistant Examiner—Lynn M. Kummert
Attorney, Agent, or Firm—Oblon, Fisher, Spivak, McClelland & Maier

[57] ABSTRACT

The present invention provides a heat exchanger using hollow fibers formed of an organic polymer as the heat transfer tubes; a blood oxygenating device comprising a blood oxygenator combined with the aforesaid heat exchanger; and a small-sized and lightweight blood oxygenator which comprises a blood oxygenator of the hollow-fiber membrane type having the aforesaid heat exchanger incorporated thereinto to form an integral unit, and hence has excellent gas exchange and heat exchange performance.

5 Claims, 4 Drawing Sheets

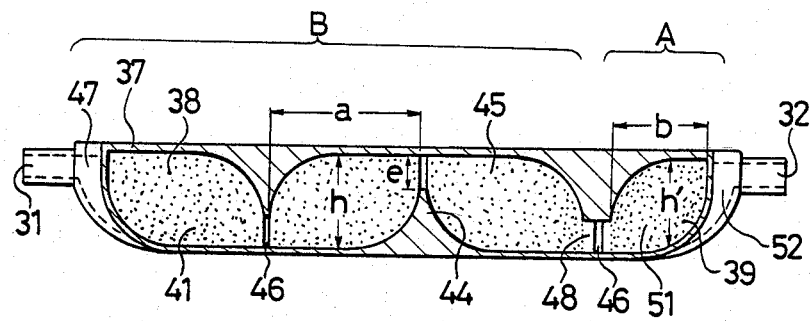
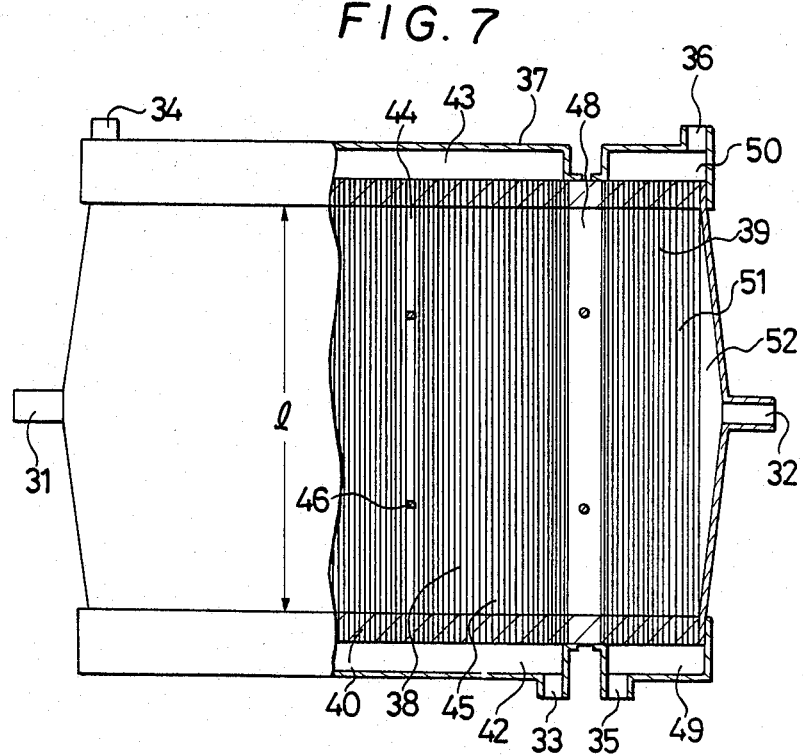

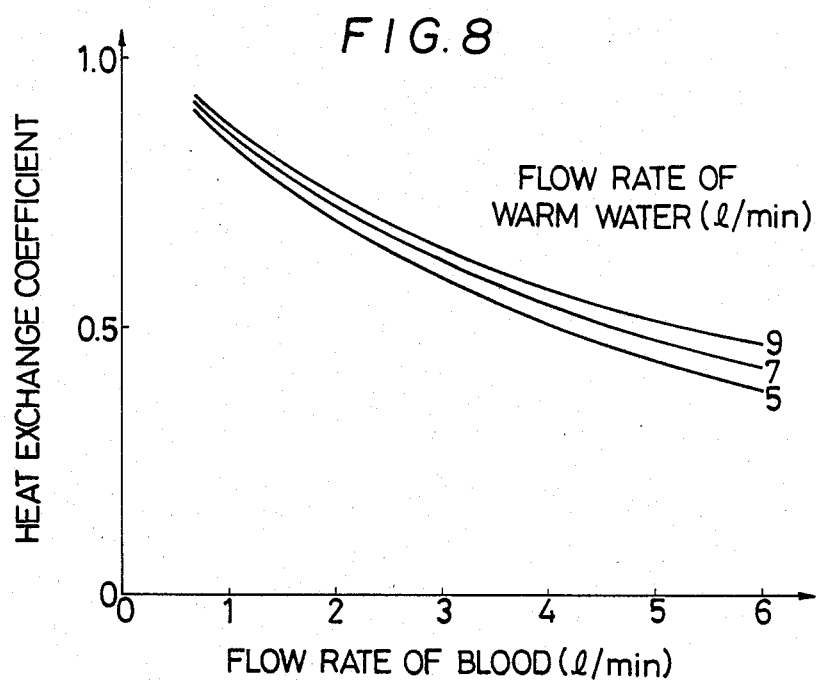
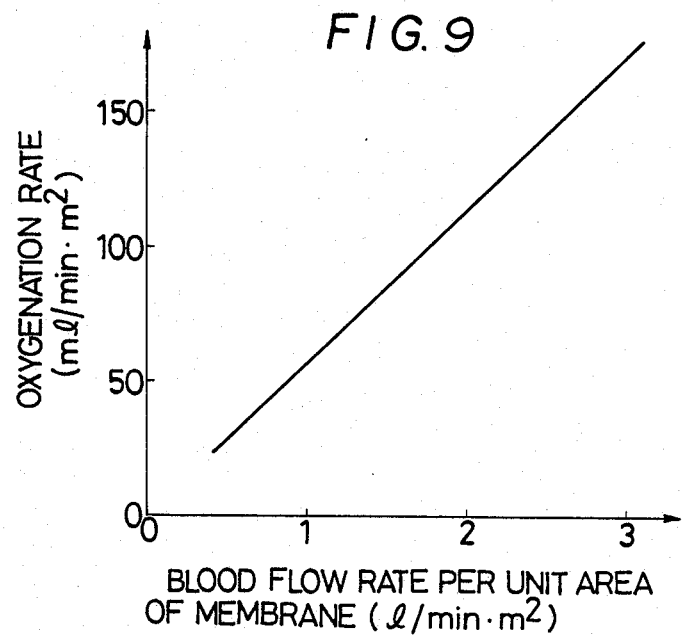

HEAT EXCHANGER AND BLOOD OXYGENATING DEVICE FURNISHED THEREWITH

This application is a continuation of application Ser. No. 699,910, filed on Feb. 8, 1985, now abandoned.

BACKGROUND OF THE INVENTION

1. Field of the Invention

This invention relates to a heat exchanger using hollow fibers made of an organic polymer as the heat transfer tubes and capable of efficiently warming or cooling various fluids including liquids such as water or blood and gases such as air, oxygen or nitrogen and to a blood oxygenating device furnished with this heat exchanger.

2. Description of the Prior Art

Conventionally, various types of heat exchangers are known as devices for transferring heat from a high-temperature fluid to a low-temperature one. Most typical heat exchangers have a multitubular construction. For use as the material of heat transfer tubes in a heat exchanger of the multitubular type, metals having good heat conductivity are most effective. Among others, stainless steel pipes have been commonly used because of their excellent resistance to corrosion by the fluids involved in heat exchange. An effective method for installing stainless pipes in a heat exchanger is potting with an organic resin, but the large difference in hardness between the stainless steel pipes and the potting material makes it difficult to process the end surfaces of the potting members. That is, the ends of the pipes have exposed sharp edges which, in the treatment of a fluid containing particles as blood cells, tend to destroy those particles. In order to overcome this difficulty, the use of stainless pipes whose tips are covered with soft pipes is under investigation, but no marked improvements have been produced.

A heat exchanger is used as a means for the heat exchange of various fluids. For example, when a blood oxygenator is used to perform an operation on the heart, a heat exchanger is usually added to the blood gas-exchange circuit including the blood oxygenator because of the necessity to adjust the body temperature of the patient to a low level at the beginning of the operation, the necessity to make the temperature of the blood having undergone gas exchange by means of the blood oxygenator almost equal to the body temperature of the patient before returning it to the body of the patient, or the necessity to restore the lowered body temperature of the patient to the normal level after the operation. In medical facilities such as hospitals and the like, this blood gas-exchange circuit is generally assembled by connecting a blood oxygenator with a separate heat exchanger by means of, for example, circuit tubes. However, such an arrangement is disadvantageous in that assemblage of the blood gas-exchange circuit is troublesome to the user, there is a risk of erroneous assemblage of the circuit, and additional space for the circuit is required. Moreover, since the blood oxygenator and the heat exchanger involves two separate stagnation sites of the blood and necessitate circuit tubes to connect them, the priming blood volume required at the initial stage of operation of the circuit is unduly large and the various circuit components must be degassed separately. Thus, such an arrangement is also complicated from the viewpoint of operation.

As means for overcoming these disadvantages, blood oxygenating device comprising a blood oxygenator combined with a heat exchanger to form an integral unit are disclosed, for example, in Japanese Patent Publication No. 2982/'80 and Japanese Patent Laid-Open No. 39854/'82. In these blood oxygenating devices, however, the heat transfer member of the heat exchange section is formed of a metal such as stainless steel having good thermal conductivity. In the case of stainless steel pipes, additional difficulties may be encountered because the metallic debris produced during processing of the pipe ends may remain in the pipes and contaminate the blood and, moreover, stainless steel may be reactive with some components of blood having a complicated composition. Accordingly, there is a continuing demand for a heat exchanger diminishing these difficulties.

On the other hand, a number of blood oxygenators using a hollow-fiber membrane have already been proposed, for example, in U.S. Pat. Nos. 2,972,349, 3,794,468, 4,239,729 and 4,374,802.

In these blood oxygenators, hollow fibers made of a homogenous membrane of gas-permeable material such as silicone or hollow fibers made of a microporous membrane of hydrophobic polymeric material such as polyolefins are used to bring blood into contact with gas through the medium of the hollow-fiber membrane and effect gas exchange therebetween. There are two types of blood oxygenators: the inside perfusion type in which blood is passed through the bores of the hollow fibers while gas is passed on the outside of the hollow fibers and the outside perfusion type in which, conversely, gas is passed through the bores of the hollow fibers while blood is passed on the outside of the hollow fibers.

In most of the conventionally known blood oxygenators, a cylindrical housing is simply packed with a large number of hollow fibers of semipermeable membrane for use in gas exchange in such a way that the hollow fibers are parallel to the axis of the cylindrical housing. However, blood oxygenators of this construction have low gas exchange rate per unit area of hollow-fiber membrane, whether they are of the inside perfusion type or of the outside perfusion type. As an improved form of the outside perfusion type, U.S. Pat. No. 3,794,468 has proposed a blood oxygenator in which hollow tubular conduits of semi-permeable membrane are wound about a hollow, cylindrical core having a large number of pores in the wall and then contained in a housing, and blood is allowed to flow out of the cavity of the core through its pores while gas is passed through the bores of the hollow tubular conduits.

In blood oxygenators of the inside perfusion type in which gas exchange is effected by passing blood through the bores of the hollow fibers while passing gas on the outside of the hollow fibers, channeling of the blood occurs less frequently. However, since the blood flowing through the bores of the hollow fibers moves in a laminar flow, the internal diameter of the hollow fibers needs to be reduced in order to increase the oxygenation rate (i.e., the oxygen transfer rate per unit area of membrane). For this purpose, hollow tubes of semipermeable membrane having an internal diameter of the order of 150–300 μm have been developed for use in blood oxygenators.

Nevertheless, as long as the blood moves in a laminar flow, the oxygenation rate cannot be greatly increased by reducing the internal diameter. Moreover, as the internal diameter becomes smaller, clotting (i.e., blockage of the bore due to the coagulation of blood) may occur more frequently and/or the blood will be more subject to hemolysis due to an increased pressure loss through the oxygenator, thus posing serious problems from a practical point of view. Furthermore, since a blood oxygenator generally uses tens of thousands of hollow fibers of semipermeable membrane made into a bundle or bundles, special consideration must be given so as to distribute the gas uniformly to the external surfaces of each of these numerous hollow fibers. If the gas is not distributed uniformly, the carbon dioxide desorption rate (i.e., the carbon dioxide transfer rate per unit area of membrane) will be reduced. On the other hand, in blood oxygenators of the outside perfusion type in which gas is passed through the bores of the hollow fibers while blood is passed on the outside of the hollow fibers, the gas can be distributed uniformly and the blood can be expected to flow turbulently. However, these oxygenators have the disadvantage of being subject to insufficient oxygenation due to channeling of the blood and/or blood coagulation at the sites of stagnation. Although the blood oxygenator of the aforementioned U.S. Pat. No. 3,794,468 has undergone improvements in this respect, it is still disadvantageous in that the priming blood volume is unduly large, a considerable pressure loss through the oxygenator is caused, and a complicated procedure is required for the manufacture thereof. Thus, it remains desirable to develop a more improved blood oxygenator.

SUMMARY OF THE INVENTION

It is an object of the present invention to provide a heat exchanger having high heat exchange efficiency in which an organic polymer that has been thought to be unsuitable for use in the material of heat transfer walls because of its low thermal conductivity is used as the heat transfer member in the form of a hollow fiber.

It is another object of the present invention to provide a heat exchanger in which the difference in hardness between the barrier member formed of an organic material and the heat transfer tubes is small enough to permit easy processing of the ends of the heat transfer tubes.

It is still another object of the present invention to provide a heat exchanger which comprises heat transfer tubes having neither exposed sharp edges at the ends thereof, nor metallic debris remaining therein, and hence is especially suitable for the treatment of liquids containing fragile particles such as blood.

It is a further object of the present invention to provide a blood oxygenating device which comprises a combination of a blood oxygenator using hollow fiber membranes as the gas exchange membrane and a heat exchanger using hollow fibers as the heat transfer tubes.

It is still a further object of the present invention to provide a blood oxygenating device which is constructed by combining a blood oxygenator having high oxygenation and carbon dioxide desorption rates and causing little stagnation or channeling of the blood with a small-sized and lightweight heat exchanger having excellent heat exchange performance to form an integral unit, and hence characterized by having a compact, low-cost and simple construction, requiring no complicated procedures during manufacture, and being easy to use.

According to one feature of the present invention, there is provided a heat exchanger comprising (1) a housing, (2) a bundle of hollow fibers made of an organic polymer, the bundle of hollow fibers being supported and packed within the housing so as to be fluid-tight at both ends thereof, (3) a heat exchange chamber formed on the outside of the hollow fibers, and (4) a fluid inlet chamber and a fluid outlet chamber provided at the respective ends of the bundle of hollow fibers in such a way as to communicate with the bores of the hollow fibers.

According to another feature of the present invention, there is provided a blood oxygenating device furnished with a heat exchanger. This blood oxygenating device has a heat exchange section for controlling the temperature of blood and a gas exchange section for effecting the gas exchange of blood, and is characterized in that (1) the heat exchange section contains a bundle of hollow fibers made of an organic polymer as the heat transfer member, the bundle of hollow fibers being supported and packed in the heat exchange section so as to be fluid-tight at both ends thereof and (2) a fluid inlet chamber and a fluid outlet chamber are provided at the respective ends of the bundle of hollow fibers in such a way as to communicate with the bores of the hollow fibers.

According to still another feature of the present invention, there is provided an improved blood oxygenating device constructed by using the internal structure of an improved blood oxygenator of the hollow-fiber membrane type as the gas exchange section of the aforesaid blood oxygenating device and containing this gas exchange section and the aforesaid heat exchange section within a single housing to form an integral unit. This blood oxygenating device comprises (1) a housing having a blood inlet, a blood outlet, a gas inlet, a gas outlet, a heat exchange medium inlet and a heat exchange medium outlet and defining therein a contact chamber, the contact chamber comprising blood flow channels narrowed by baffles and a plurality of compartments separated by the blood flow channels, (2) a first bundle or bundles of hollow fiber membranes consisting of a large number of hollow fiber membranes for use in gas exchange and having fixed ends, and (3) a second bundle or bundles of hollow fibers consisting of a large number of hollow fibers for use in heat exchange and having fixed ends, the first and second bundles of hollow fiber membranes being disposed in separate compartments so as to be substantially parallel to said baffles, the respective ends of the first bundle of hollow fiber membranes communicating with the gas inlet and the gas outlet and the respective ends of the second bundle of hollow fiber membranes communicating with the heat exchange medium inlet and the heat exchange medium outlet.

BRIEF DESCRIPTION OF THE DRAWINGS

FIG. 6 is a vertical sectional view of a preferred embodiment of the blood oxygenating device furnished with a heat exchanger in accordance with the present invention;

FIG. 7 is a partially cutaway plan view of the blood oxygenating device of FIG. 6;

FIG. 8 is a graph showing the heat exchange performance of the blood oxygenating device of the present invention; and FIG. 9 is a graph showing the oxygenation performance of the blood oxygenating device of the present invention.

DETAILED DESCRIPTION OF THE PREFERRED EMBODIMENTS

The construction of a heat exchanger in accordance with the present invention will now be described with reference to FIG. 1.

Figure 1:
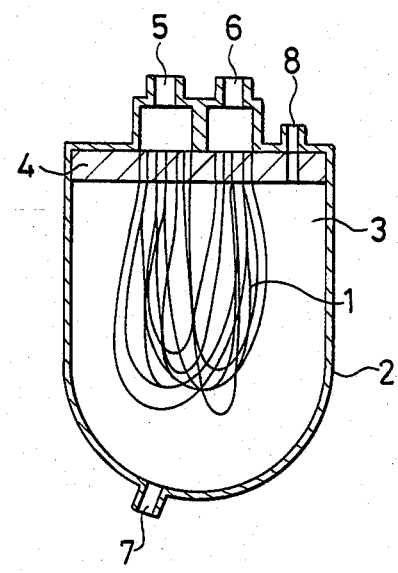
FIG. 1 is a schematic sectional view of a heat exchanger in accordance with the present invention.

As shown in FIG. 1, this heat exchanger comprises hollow fibers 1 for use in heat exchange, a housing 2 for containing the hollow fibers, and a heat exchange chamber 3. A barrier member 4 serves to separate the heat exchange chamber 3, in a fluid-tight manner, from the open ends of the hollow fibers 1 and from a fluid inlet (or outlet) chamber 5 and a fluid outlet (or inlet) chamber 6 which both communicate with the cavities of the hollow fibers. The heat exchanger also has a fluid inlet 7 and a fluid outlet 8 which both communicate with the heat exchange chamber 3.

Figure 2:
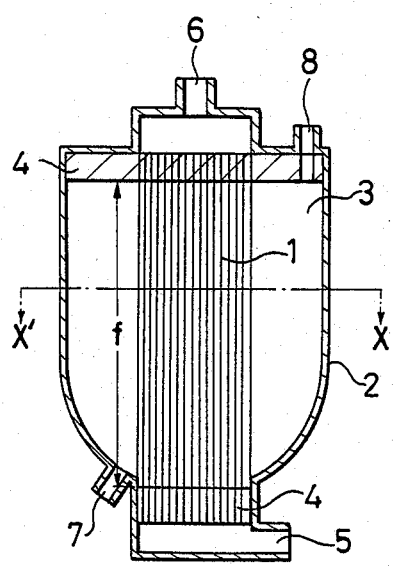
FIGS. 2 and 3 are schematic sectional views of other embodiments of the heat exchanger of the present invention.
Figure 3:
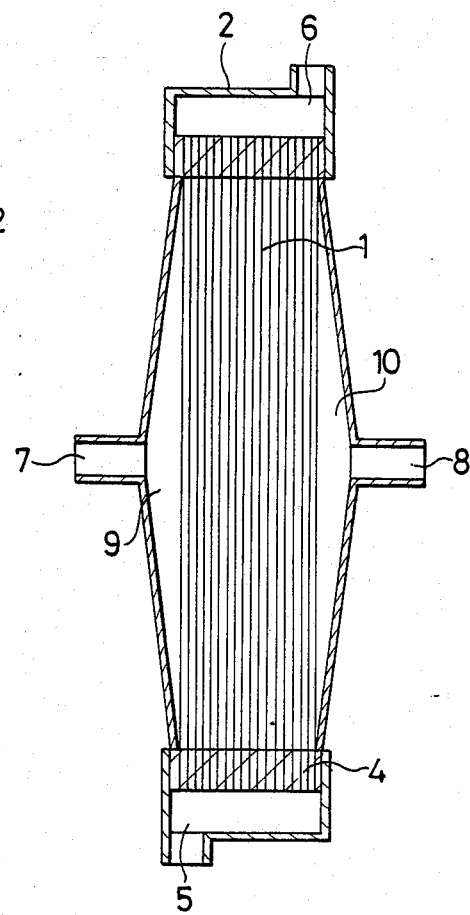

Referring to FIGS. 2 and 3, there are shown other embodiments of the heat exchanger of the present invention. Unlike the heat exchanger of FIG. 1, these embodiments have a bundle of hollow fibers 1 disposed in straight lines within a housing 2. In the embodiment of FIG. 3, a fluid distribution chamber 9 and a fluid collection chamber 10 are provided between the fluid inlet 7 and the region occupied by the hollow fibers 1 and between the fluid outlet 8 and the region occupied by the hollow fibers 1, respectively, in order that the fluid flowing on the outside of the hollow fibers 1 may follow flow paths substantially perpendicular to the hollow fibers 1.

In making the heat exchanger of the present invention, the material of the hollow fibers constituting heat transfer tubes may be selected from a variety of organic polymers. Examples thereof include polyolefins and fluorinated polyolefins such as polypropylene, polyethylene, poly-4-methyl-1-pentene, polyvinylidene fluoride, and polytetrafluoroethylene; acrylonitrile polymers; cellulosic polymers; polyamides and polyimides; polyesters; silicone resins; polymethyl methacrylate and its analogs; polycarbonates; and polysulfones. Among others, organic polymers having a thermal conductivity of $1.0 \times 10^{-5}$ to $50.0 \times 10^{-4}$ cal/cm.sec.°C. can be used to make a plastic heat exchanger which compares favorably in heat exchange efficiency with conventional heat exchangers using metallic pipes.

Moreover, in order to enhance the heat transfer efficiency of the heat exchanger of the present invention, it is preferable to use hollow fibers having an internal diameter of about 50 to 1,000 $\mu$m and a wall thickness of about 2 to 200 $\mu$m.

If the internal diameter of the hollow fibers used is excessively small, a large pressure loss may be caused during operation and the sealability of the fluid paths will be reduced. On the other hand, if the internal diameter of the hollow fibers is excessively large, the fluid flowing through the bores of the hollow fibers will have a small heat transfer coefficient and the relative volume occupied by the hollow fibers per unit heat transfer area will be increased, resulting in a reduction in heat transfer efficiency and resulting in enlargement in the size of the heat exchanger. Moreover, the wall thickness of the hollow fibers should desirably be as thin as possible, with a view to decreasing their heat transfer resistance and making it possible to form a heat exchanger of compact size. However, it is most preferable from the viewpoint of strength and handleability that the hollow fibers used in the present invention should have an internal diameter of 150 to 500 $\mu$m and a wall thickness of 10 to 100 $\mu$m.

In the embodiment shown in FIG. 1, the heat exchanger of the present invention can be assembled by providing hollow fibers 1 made of an organic polymer as described above and disposing them in a housing 2. After a barrier member 4 is formed using a potting material selected from, for example, epoxy resins, unsaturated polyester resins, and polyurethane resins, the end surface of the barrier member 4 is processed in such a way that the hollow fibers have open ends. Finally, a fluid inlet chamber 5 and a fluid outlet chamber 6 are provided.

The heat exchanger of the present invention permits easy processing of the end surface of the barrier member because the difference in hardness between the barrier member and the hollow fibers is very small as compared with heat exchangers using metallic pipes as the heat transfer member. Thus, the open ends of the hollow fibers are so smooth that, even when this heat exchanger is used for the treatment of blood, the bood cells contained in the blood are by no means damaged by any edge formed at the ends of the hollow fibers. Moreover, the heat exchange efficiency of this heat exchanger can stand comparison with that of heat exchangers using metallic pipes.

Now, the blood oxygenating device furnished with a heat exchanger in accordance with the present invention will be more fully described with reference to the accompanying drawings.

The blood oxygenating device furnished with a heat exchanger in accordance with the present invention constitutes a heat exchange section A for performing the function of heat exchange with blood and a gas exchange section B for performing the function of gas exchange with blood. The heat exchange section A can be of the inside perfusion type in which blood is passed through the bores of the hollow fibers for use in heat exchange, or of the outside perfusion type in which blood is passed on the outside of the hollow fibers for use in heat exchange. The embodiment shown in FIG. 4 is of the inside perfusion type, while that shown in FIG. 5 is of the outside perfusion type.

Figure 4:
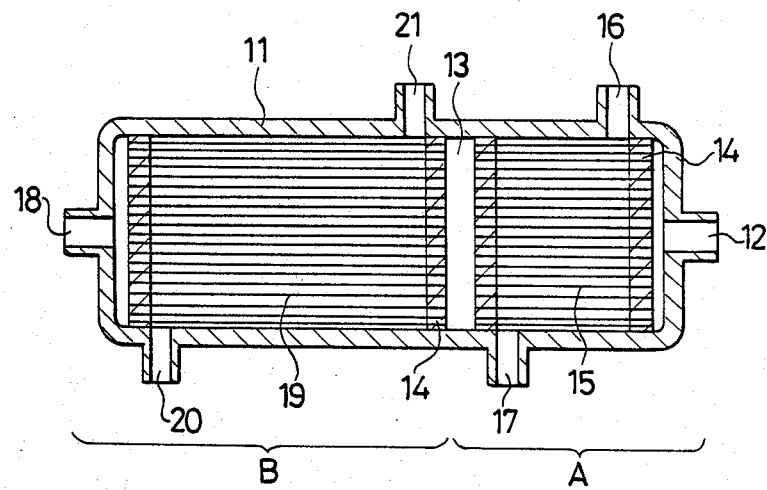
FIG. 4 is a schematic sectional view of a blood oxygenating device furnished with a heat exchanger in accordance with the present invention.
Figure 5:
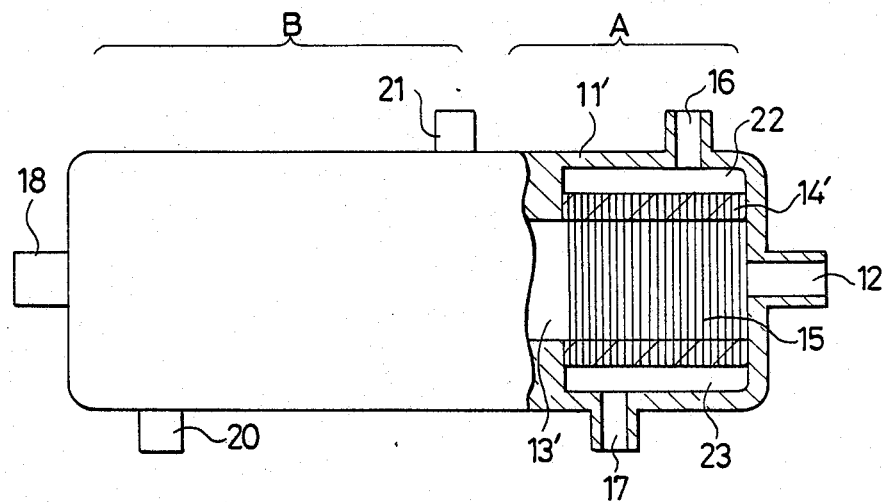
FIG. 5 is a partially cutaway plan view of another embodiment of the blood oxygenating device of the present invention.

The heat exchange section A of the inside perfusion type shown in FIG. 4 comprises a housing 11, a blood inlet (or outlet) 12, a blood flow channel 13, hollow fibers 15 for use in heat exchange, potting members 14 for fastening the hollow fibers 15 within the housing 11 and separating the flow space for heat exchange medium from the flow space for blood, a heat exchange medium inlet(or outlet)16 and a heat exchange medium outlet (or inlet) 17. Where blood is passed through the heat exchange section A and the gas exchange section B in this order, the blood fed to the blood inlet 12 flows through the bores of the hollow fibers 15 for use in heat exchange and undergoes heat exchange with the heat exchange medium fed to the heat exchange medium inlet 16 and passed on the outside of the hollow fibers 15 for use in heat exchange. Then, the blood traverses the blood flow channel 13 and enters the gas exchange section B, where it undergoes gas exchange. Thus, the temperature-controlled oxygenated blood emerges from the blood outlet 18.

In the blood oxygenating device of FIG. 4, the gas exchange section B is constructed so as to be of the inside perfusion type in which blood is passed through the bores of the hollow fiber membrane 19 for gas exchange. An oxygen-containing gas is introduced through the gas inlet 20 into the gas exchange section B, where it undergoes gas exchange with the blood flowing through the bores of the hollow fiber membrane 19 for use in gas exchange, through the medium of the hollow fiber membrane. The gas thus decreased in oxygen content and increased in carbon dioxide content is discharged from the gas outlet 21.

In the blood oxygenating device of FIG. 4, blood may first be subjected to gas exchange and then to heat exchange. This can be accomplished by feeding the blood through the blood outlet 18 and withdrawing it from the blood inlet 12.

In the blood oxygenating device of the outside perfusion type shown in FIG. 5, the heat exchange section A differs from that of FIG. 4 only in that the blood does not flow through the bores of the hollow fibers 15 for use in heat exchange, but flows on the outside thereof. The heat exchange medium fed through the heat exchange medium inlet 16 (or 17) passes through the heat exchange medium flow passage 22 (or 23) formed between the housing 11' and the potting member 14', through the bores of the hollow fibers, and they through the other heat exchange medium flow passage 23 (or 22). Thereafter, the heat exchange medium is discharged from the heat exchange medium outlet 17 (or 16).

In the heat exchange section A of the blood oxygenating device of the present invention, the hollow fibers for use in heat exchange and the potting members may be made of the same material as described above in connection with the heat exchanger of the present invention. Moreover, the heat exchange section A may be made in the same manner as described in connection with the heat exchanger.

In the gas exchange section B of the blood oxygenating device of the present invention, any of various types of blood oxygenators such as conventionally known membrane type blood oxygenators and bubble type blood oxygenators may be installed. However, membrane type blood oxygenators and, in particular, those using a hollow-fiber membrane are preferred.

Since the blood oxygenating device of the present invention has an integrally formed heat exchanger, no circuit tubes or similar communicating devices are needed to connect the blood oxygenator with the heat exchanger, assemblage and operation of the circuit are easy, and the priming blood volume required at the initial stage of operation is small. Furthermore, the blood oxygenating device of the present invention has further advantages in that processing of the heat transfer tubes is easy because metal tubes are not employed, the blood cells contained in the blood suffer almost no damage, and it is small-sized and lightweight.

Now, the blood oxygenating device of the present invention will be more fully described in connection with the most preferred embodiment in which the gas exchange section constitutes the internal structure of an improved membrane type blood oxygenator and both the gas exchange section and the heat exchange section are contained within a single housing.

FIG. 6 is a vertical sectional view of such a blood oxygenating device, and FIG. 7 is a partially cutaway plan view thereof. This blood oxygenating device has a blood inlet 31, a blood outlet 32, a gas inlet 33, a gas outlet 34, a heat exchange medium inlet 35 and a heat exchange medium outlet 36, and includes a gas exchange section B and a heat exchange section A contained within a housing 37 generally in the form of a box. The gas exchange section B comprises compartments each having disposed therein a bundle of hollow fibers 38 for use in gas exchange and performs the function of gas exohange with blood, and the heat exchange section A comprises a compartment (or heat exchange chamber) having disposed therein a bundle of hollow fibers 39 for use in heat exchange and performs the function of heat exchange with blood, both sections being directly connected without the aid of tubes or similar communicating devices.

Basically, the gas exchange section B includes hollow fiber membranes 38 for use in gas exchange and potting members (or barrier members) 40. These members cause the internal space of the gas exchange section B to be divided into a contact chamber 41 through which blood flows, a gas distribution passage 42 for feeding an oxygen-containing gas to the bores of the hollow fiber membranes 38, and a gas collection passage 43 for conducting the gas to the gas outlet 34. The contact chamber 41 includes a plurality of baffles 44 disposed transversely to the flow of the blood so as to narrow the blood flow path in a direction perpendicular to that of the hollow fiber membranes (hereinafter referred to as the direction of the thickness of the contact chamber), and these baffles cause the contact chamber 41 to be divided into a plurality of compartments 45 containing hollow fiber membranes 38. On the baffles 44, one or more struts 46 may be provided in such a way as to extend in the direction of the thickness of the contact chamber 41.

The hollow fiber membranes 38 are disposed substantially in straight lines within the compartments 45 and fastened with two opposite potting members 40 in such a way that their respective ends remain open to the gas distribution channel 42 and the gas collection channel 43.

In the gas exchange section B of this blood oxygenating device, an oxygen-containing gas is fed to the gas distribution passage 42 through the gas inlet 33 and then passed through the bores of the hollow fiber membrane 38 disposed in the contact chamber 41, where it undergoes gas exchange with the blood through the medium of the hollow fiber membrane. The gas thus decreased in oxygen content and increased in carbon dioxide content is conducted to the gas collection passage 43 and then discharged from the gas outlet 34. Of course, the oxygen-containing gas fed through the gas inlet 33 may comprise pure oxygen.

On the other hand, blood withdrawn from a human body (i.e., venous blood) is introduced into the blood flow uniforming chamber 47 through the blood inlet 31 and then passed through the contact chamber 41, where it undergoes gas exchange, through the medium of the hollow fiber membrane, with the oxygen-containing gas flowing through the bores of the hollow fibers 38. Thus, the venous blood is converted into arterial blood, which is fed to the heat exchange section A by way of the blood flow channel 48 connecting the gas exchange section B with the heat exchange section A.

In the embodiment shown in FIG. 6, the contact chamber is divided into three compartments 45 by two baffles 44. However, there may be present any desired number of compartments 45, provided the number of compartments 45 is not less than 2. Although greater numbers are more preferable, it is practicably desirable in view of the ease of manufacture to divide the contact chamber into 2 to 6 compartments.

The baffles 44 may have any of various cross-sectional shapes, provided that they can narrow the blood flow channel in the direction of the thickness of the contact chamber. However, baffles having a curved cross section as shown in FIG. 6 are preferably used in order to avoid stagnation the blood. The baffles 44 provided in the contact chamber 41 serve not only to prevent channeling of the blood flow in the direction of the thickness, but also to make uniform the oxygen and carbon dioxide contents of the blood in cross sections perpendicular to the direction of the blood flow and thereby achieve good gas exchange.

As shown in FIG. 6, the manner in which the blood flow channel is narrowed by the baffles 44 in the direction of the thickness of the contact chamber should preferably be such that adjacent baffles 44 are alternately positioned on the upper and lower walls.

The dimensions of the contact chamber 41 in the blood oxygenating device of the present invention will now be described hereinbelow. It is preferable that the length (a) of each compartment 45 as measured in the direction of blood flow be larger than the maximum thickness (h) of the compartment. If the thickness (h) is larger than the length (a), the flow of blood in the direction of the thickness will be so dominant that stagnation of the blood will tend to occur at the corners of the compartment (i.e., in the vicinity of the boundaries between the compartment and the narrowed blood flow channels) and entrained air bubbles can hardly be removed when air bubbles are entrained. In order to obtain the effects of the baffles 44, the thickness (e) of the blood flow channels narrowed by the baffles 44 is preferably equal to or smaller than one-half the thickness (h) of the compartments.

The width (l) of the contact chamber 41 (i.e., the distance between the two potting members 40) should be appropriately determined in relation to the flow rate of blood and the thickness (h) of the compartments. However, in order to produce a desirable sheet-like flow of blood in the contact chamber, it is preferable that the width (l) of the contact chamber be about 1 to 20 times as large as the thickness (h) of the contact chamber. If the width (l) is smaller than the thickness (h), the surfaces of the potting members will exert a significant effect on the blood flow and, occasionally result in poor workability. If the width (l) is larger than 20 times the thickness (h), it will become difficult to some extent to distribute the blood uniformly over the surfaces of all hollow fibers and thereby prevent channeling of the blood.

In the contact chamber, the hollow fibers are disposed almost perpendicularly to the direction of blood flow. The term "direction of blood flow" as used herein does not mean the direction of the blood flow actually produced by passing blood through the contact chamber, but the direction of the straight line connecting the blood inlet with the blood outlet. In order to prevent channeling of the blood, the hollow fibers need to form an angle of at least 45° with the direction of blood flow, and it is most preferable that the hollow fibers be almost perpendicular to the direction of blood flow. The reason for this is believed to be that, when the blood flows across the hollow fibers, small turbulences of the blood flow are produced around the hollow fibers. Moreover, the large number of hollow fibers contained in each compartment are preferably disposed in such a way that each hollow fiber is parallel to the longitudinal axis of the bundle of hollow fibers. However, they may be disposed in such a way that a plurality of hollow fibers are bundled and they are wound at an angle of up to 45° with the longitudinal axis of the bundle of hollow fibers.

The degree of packing of the hollow fibers contained in each compartment preferably ranges from 10% to 55%. The term "degree of packing" as used herein means the proportion of the total cross-sectional area of the hollow fibers to the cross-sectional area of the compartment, as viewed in a plane perpendicular to the direction of blood flow in the contact chamber. If the degree of packing is less than 10%, channeling of the blood will tend to occur and turbulence of the blood flow can hardly be produced. If the degree of packing is greater than 55%, the flow resistance of the blood will become unduly high and hemolysis may be induced. Although the degree of packing of the hollow fibers may vary with the compartment, it is preferable for convenience of manufacture to employ an equal degree of packing for all compartments.

The hollow fibers contained in the blood oxygenating device for use in gas exchange may comprise hollow fibers made of various homogeneous or porous membrane materials including, for example, cellulosics, polyolefins, polysulfones, polyvinyl alcohol, silicone resins and PMMA. However, hollow fibers made of a porous polyolefin membrane are preferred because of their excellent durability and gas permeability. Especially preferred are hollow fibers formed of a membrane which comprises fibrils stacked in layers between both surfaces and nodes fixing the respective ends of the fibrils and, therefore, has micropores composed of the spaces between the fibrils and interconnected so as to extend from one surface to the other. Examples of such hollow fibers include polypropylene hollow fibers and polyethylene hollow fibers, both commercially available from Mitsubishi Rayon Co., Ltd. under the trade name of KPF and EHF, respectively.

Struts 46 which may be provided on the baffles 44 can perform the functions of producing turbulences of the blood flow in the contact chamber and preventing the hollow fibers contained in the compartments from being moved toward the baffles by the blood flow to give an unduly high degree of packing of the hollow fibers in these regions and thereby induce hemolysis or the like. Accordingly, it is a preferred embodiment of the present invention to provide such struts 46.

The potting members 40 may be conveniently formed in the same manner as in the manufacture of so-called hollow-fiber filtration modules using hollow fibers. Specifically, this can be accomplished by selecting a potting material having good adhesion properties from polyurethane, unsaturated polyesters, epoxy resins and the like, and molding it integrally with the hollow fibers.

On the other hand, the heat exchange section A has provided therein a heat exchange medium inlet 35, a heat exchange medium distribution passage 49, a bundle of hollow fibers 39 for use in heat exchange, a heat exchange medium collection passage 50 and a heat exchange medium outlet 36. The bundle of hollow fibers 39 for use in heat exchange, which allows a heat exchange medium such as warm water to flow through the bores thereof, is disposed almost perpendicularly to the direction of the blood flowing from the blood flow channel 48 to the blood outlet 32. When the hollow fibers 39 are disposed in this manner, the heat transfer resistance of the laminar film of blood can be reduced and the heat exchange efficiency between the blood and the heat exchange medium can be enhanced, thus making it possible to form a heat exchange section A of compact size.

In the embodiment shown in FIGS. 6 and 7, the heat exchange chamber 51 containing the bundle of hollow fibers 39 for use in heat exchange comprises only one compartment. However, similar to the gas exchange section B, the heat exchange chamber may be divided into a plurality of compartments. Moreover, although this embodiment is constructed so that the blood passes through the gas exchange section B and the heat exchange section A in this order, it is also possible to subject the blood to heat exchange in the heat exchange section B and then to gas exchange in the gas exchange section B. Furthermore, the bundles of hollow fibers for use in heat exchange and ones for use in gas exchange may be disposed in any desired compartments of the contact chamber of the blood oxygenating device of the present invention in order to subject the blood to gas exchange and heat exchange in any desired order.

This improved type of blood oxygenating device furnished with a heat exchanger not only has the previously described advantages of the exchanger of the present invention, but also can exhibit the additional beneficial effect of achieving high oxygenation and carbon dioxide desorption rates per unit area of the hollow fiber membrane (even if the blood is passed with a low pressure loss) because little stagnation or channeling of the blood is caused and turbulence of the blood flow is produced easily.

The present invention is further illustrated by the following examples.

EXAMPLE 1

A water-water heat exchange test was carried out using a heat exchanger of the construction shown in FIG. 2. The hollow fibers used in this heat exchanger were made of high-density polyethylene and had an internal diameter of 360 $\mu$m and a wall thickness of 20 $\mu$m. The effective heat transfer length (f) of the hollow fibers was 10 cm, their effective heat transfer area was 0.1 m$^2$, and their degree of packing (i.e., the proportion of the total cross-sectional area of the hollow fibers to that of the housing as viewed in the cross section taken along the line X—X' of FIG. 2) was 17%.

Specifically, water having a temperature of 30° C. was fed through the fluid inlet at each flux shown in Table 1, while warm water having a temperature of 40° C. was passed through the heat exchange chamber. Thus, the temperature of the water emerging from the fluid outlet was examined.

TABLE 1

| Flux of water (liters/min) | fluid temperature at fluid outlet |
| --- | --- |
| 1.0 | 37.2° C. |
| 2.0 | 36.4° C. |

It is to be understood that the water temperature at the fluid outlet can be adjusted to any desired value by appropriately determining the inlet temperature and flow rate of the water being passed through the heat exchange chamber.

EXAMPLE 2

A blood oxygenator of the construction shown in FIGS. 6 and 7 was assembled. The gas exchange section B comprised three compartments having a thickness (h) of 4.0 cm, a length (a) of 4.0 cm and a width (l) of 13 cm, which compartments were separated by two blood flow channels narrowed by baffles and having a thickness (e) of 1 cm and a length of 0.5 cm. In each of these compartments, hollow fibers for use in gas exchange were packed so as to give a degree of packing of 25%. The hollow fibers used were hollow fibers made of a porous polypropylene membrane (commercially available from Mitsubishi Rayon Co., Ltd. under the trade name of KPF) and characterized by a wall thickness of 22 $\mu$m, an internal diameter of 200 $\mu$m and a bubble point of 12.5 kg/cm$^2$. The total surface area of the membrane as calculated on the basis of the internal diameter was 2.0 m$^2$. The heat exchange section A comprised a heat exchange chamber having a thickness (h') of 4.0 cm, a length (b) of 3.0 cm and a width (l) of 13 cm, in which the same hollow fibers as used in Example 1 (were packed so as to give a degree of packing of 25% with a heat transfer area of 0.25 m$^2$ as calculated on the basis of the internal diameter). The gas exchange section B and the heat exchange section A were connected by a blood flow channel having a thickness of 1 cm and a length of 1 cm.

Using this blood oxygenator, a heat exchange test was carried out on bovine blood which had previously been adjusted to 30° C. The bovine blood had a hematocrit of 35%, a pH of 7.32, an oxygen partial pressure of 65 mmHg, a carbon dioxide partial pressure of 45 mmHg and a hemoglobin concentration of 12.5 g/dl.

Specifically, the bovine blood was fed through the blood inlet 31 at various flow rates, while pure oxygen having a temperature of 30° C. was fed through the gas inlet 33 at flow rate of 10 liter/min. Separately, warm water having a temperature of 36°, 38° and 40° C. was fed through the heat exchange medium inlet 35 at each of the flow rates of 5, 7 and 9 liter/min. Thus, the temperature of the blood emerging from the blood outlet 32 was measured.

The results obtained with warm water having a temperature of 40° C. are shown in FIG. 8. When the warm water had a temperature at 36° C. or 38° C., the results obtained were substantially the same as shown in FIG. 8. As can be seen from these results, the temperature of the blood emerging from the blood outlet can be adjusted to any desired value by varying the temperature and flow rate of the heat exchange medium. In FIG. 8, the coefficient of heat exchange is defined by the following equation:

$$\text{Coefficient of heat exchange} = \frac{(\text{outlet temperature of blood}) - (\text{inlet temperature of blood})}{(\text{inlet temperature of warm water}) - (\text{inlet temperature of blood})}$$

In addition, the same procedure was repeated except that the bovine blood and oxygen were adjusted to 37°

C. and the blood flow rate per unit area of membrane (Q/S) was varied from 0 to 3 liters/m².min. Thus, the oxygen partial pressure of the blood emerging from the blood outlet was measured to determine the oxygenation rate (in ml/min.m²) of this blood oxygenator.

The results thus obtained are shown in FIG. 9.

What is claimed is:

1. A method of oxygenating blood in a blood oxygenating device of the outside perfusion type which has a heat exchange section for controlling the temperature of blood and a gas exchange section for effecting the gas exchange of blood, wherein, in one housing, a blood flow path of the heat exchange section is connected with a blood flow path of the gas exchange section, comprising:

passing blood to be oxygenated through said heat exchange section containing a bundle of linearly extending hollow fibers made of an organic polymer as the heat transfer medium, through which fibers a heat exchange fluid flows, said bundle of hollow fibers being supported and packed in said heat exchange section so as to be fluid-tight at both ends thereof, and said heat exchange section having a heat exchange fluid inlet chamber and a heat exchange fluid outlet chamber provided at respective ends of said bundle of hollow fibers of said heat exchange section in such a way as to communicate with the bores of said hollow fibers, said blood flowing through the heat exchange section in a direction substantially perpendicular to the bundle of hollow fibers of said heat exchange section, and;

passing blood to be oxygenated through said gas exchange section, said gas exchange section having a plurality of compartments each containing a bundle of linearly extending hollow fibers as the gas exchange medium, through which fibers an oxygenating gas flows, said compartments being separated by blood flow channels narrowed by baffles, said bundle of hollow fibers of said gas exchange section being supported and packed in said compartments so as to be substantially parallel to said baffles and to be fluid-tight at both ends thereof, and said gas exchange section having a gas inlet chamber and a gas outlet chamber provided at respective ends of said bundle of hollow fibers of said gas exchange section in such a way as to communicate with the bores of said hollow fibers, said blood flowing through said compartments in a direction substantially perpendicular to the bundle of hollow fibers of said gas exchange section.

2. A method of oxygenating blood in a blood oxygenating device of the outside perfusion type which has a gas exchange section for effecting the gas exchange of blood and a heat exchange section for controlling the temperature of blood, and, in one housing, a blood flow path of the gas exchange section is connected with a blood flow path of the heat exchange section, comprising:

passing blood to be oxygenated through said gas exchange section, said gas exchange section having a plurality of compartments each containing a bundle of linearly extending hollow fibers as the gas exchange medium, through which fibers an oxygenating gas flows, said compartments being separated by blood flow channels narrowed by baffles, said bundle of hollow fibers of said gas exchange section being supported and packed in said compartments so as to be substantially parallel to said baffles and to be fluid-tight at both ends thereof, and said gas exchange section having a gas inlet chamber and a gas outlet chamber provided at respective ends of said bundle of hollow fibers of said gas exchange section in such a way as to communicate with the bores of said hollow fibers, said blood flowing through said compartments in a direction substantially perpendicular to the bundle of hollow fibers of said gas exchange section, and;

passing oxygenated blood through said heat exchange section containing a bundle of linearly extending hollow fibers made of an organic polymer as the heat transfer medium, through which fibers a heat exchange fluid flows, said bundle of hollow fibers of said heat exchange section being supported and packed in said heat exchange section so as to be fluid-tight at both ends thereof, and said heat exchange section having a heat exchange fluid inlet chamber and a heat exchange fluid outlet chamber provided at respective ends of said bundle of hollow fibers of said heat exchange section in such a way as to communicate with the bores of said hollow fibers, said blood flowing through the heat exchange section in a direction substantially perpendicular to the bundle of hollow fibers of said heat exchange section.

3. A blood oxygenator of the hollow fiber membrane type having a heat exchanger incorporated thereinto, which comprises (1) a housing having a blood inlet, a blood outlet, a gas inlet, a gas outlet, a heat exchange medium inlet and a heat exchange medium outlet and defining therein a contact chamber, said contact chamber comprising blood flow channels narrowed by baffles and a plurality of compartments separated by said blood flow channels (2) a first bundle or bundles of hollow fibers consisting of a large number of hollow fibers for use in gas exchange and having fixed ends, and (3) a second bundle or bundles of hollow fibers consisting of a large number of hollow fibers for use in heat exchange and having fixed ends, said first and second bundles of hollow fibers being disposed in separate compartments so as to be substantially parallel to said baffles, the respective ends of said first bundle of hollow fibers communicating with said gas inlet and said gas outlet and the respective ends of said second bundle of hollow fibers communicating with said heat exchange medium inlet and said heat exchange medium outlet.

4. The blood oxygenator of claim 3 wherein said hollow fibers for use in heat exchange have an internal diameter of 5 to 1,000 μm and a wall thickness of 2 to 200 μm.

5. The blood oxygenator of claim 3:

wherein the housing is generally in the form of a box and has a blood-gas contact chamber therein, said chamber having an entrance in communication with said blood inlet and an exit in communication with said blood outlet, said chamber having an overall length as measured in a direct line between said entrance and said exit, an overall width measured in a direction perpendicular to said direct line, and an overall thickness measured in a direction perpendicular to both said overall length and said overall width;

wherein said first bundle or bundles of semipermeable hollow fibers are disposed in said chamber, said hollow fibers being made of a material suitable for the oxygenation of blood;

wherein said second bundle or bundles of hollow fibers are disposed in said chamber, said hollow fibers being made of an organic polymer suitable for the heat exchange of blood; and section of a potting material respectively securing together opposite ends of said fibers of said first bundle or bundles in such a way as to allow open ends thereof to communicate respectively with said gas inlet and said gas outlet, and respectively securing together opposite ends of said fibers of said second bundle or bundles in such a way as to allow open ends thereof to communicate respectively with said heat exchange medium inlet and said heat exchange medium outlet, said sections of potting material being disposed on two opposite sides of said chamber, extending substantially in the direction of said overall length and establishing said overall width of said chamber as being the distance across said chamber between said sections of potting material, a space around said first and second bundles communicating with said blood inlet and said blood outlet, said chamber being divided into a plurality of compartments by the interposition of at least one baffle projecting into said chamber to form a narrow blood flow channel, said at least one baffle projecting into said chamber substantially in the direction of the thickness of said chamber and also extending in a direction substantially parallel to said first or said second bundle or bundles, said first and said second bundle or bundles of hollow fibers each being disposed in a separate one of said plurality of compartments, wherein the length of each of said plurality of compartments as measured in the direction of said overall length of said chamber is equal to or greater than the maximum thickness of each of said plurality of compartments as measured in the direction of said thickness of said chamber.

* * * * *